(12) United States Patent
Ruscher

(10) Patent No.: US 6,770,064 B1
(45) Date of Patent: Aug. 3, 2004

(54) INTERNALLY HEATED ABSORBENT ARTICLE

(75) Inventor: Edward Herman Ruscher, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/707,259

(22) Filed: Nov. 6, 2000

Related U.S. Application Data

(60) Division of application No. 09/133,438, filed on Aug. 13, 1998, now abandoned, which is a continuation-in-part of application No. 08/854,876, filed on May 12, 1997, now abandoned.
(60) Provisional application No. 60/033,987, filed on Dec. 30, 1996.

(51) Int. Cl.[7] .............................. A61F 13/15; A61F 13/20
(52) U.S. Cl. .................... 604/385.01; 604/367
(58) Field of Search .................... 604/358, 367, 604/378–380, 385.01, 386, 387, 291, 385.63, 385.17, 385.18, 361, 364; 602/2, 14, 67–73; 607/108–114, 96; 128/885, 886

(56) References Cited

U.S. PATENT DOCUMENTS

| | | | |
|---|---|---|---|
| 1,892,389 A | 12/1932 | Evans | |
| 1,899,286 A | 2/1933 | Meagher | |
| 2,573,791 A | 11/1951 | Howells | |
| 3,794,029 A | * 2/1974 | Dulle | |
| 3,913,559 A | 10/1975 | Dandliker | 126/263 |
| 3,921,232 A | * 11/1975 | Whyte | |
| 3,976,049 A | 8/1976 | Yamashita et al. | 126/263 |
| 4,106,477 A | 8/1978 | Feld | 126/263 |
| 4,331,731 A | 5/1982 | Seike et al. | 428/305.5 |
| 4,397,315 A | 8/1983 | Patel | 128/403 |
| 4,573,447 A | 3/1986 | Thrash et al. | 126/263 |
| 4,639,949 A | * 2/1987 | Ales et al. | 2/400 |
| 4,747,841 A | 5/1988 | Kuratomi et al. | 604/291 |
| 4,756,299 A | 7/1988 | Podella | 126/263 |
| 4,925,743 A | 5/1990 | Ikeda et al. | 428/702 |
| 4,931,608 A | 6/1990 | Bills | 219/10.55 F |
| 4,940,464 A | * 7/1990 | Van Gompel et al. | 604/396 |
| 5,046,479 A | 9/1991 | Usui | 126/204 |
| 5,167,655 A | 12/1992 | McCoy | 604/396 |
| 5,178,139 A | 1/1993 | Angelillo et al. | 128/403 |
| 5,187,814 A | 2/1993 | Gold | 2/160 |
| 5,277,180 A | 1/1994 | Angelillo et al. | 607/114 |

(List continued on next page.)

FOREIGN PATENT DOCUMENTS

| | | |
|---|---|---|
| DE | 1491138 | 2/1969 |
| EP | 0 368 544 A1 | 5/1990 |
| EP | 0 704 195 A2 | 3/1996 |
| FR | 1.518.000 | 3/1968 |
| GB | 1 383 536 | 2/1975 |
| GB | 2 297 490 | 8/1996 |
| JP | 59-540 | 1/1984 |
| JP | 60-222052 | 11/1985 |
| JP | 62-347 | 1/1987 |
| JP | 5-208031 | 8/1993 |
| WO | 94/03132 | 2/1994 |
| WO | 96/19172 | 6/1996 |
| WO | 97/36968 | 10/1997 |
| WO | 98/29079 | 7/1998 |

OTHER PUBLICATIONS

Gupta, B.S. and A.L. Crews, "The Effect of Fluid Characteristics on Absorbency in Nonwovens," Nonwovens—An Advanced Tutorial, Tappi Press, 1989, pp. 197–218.

*Primary Examiner*—Karin Reichle
(74) *Attorney, Agent, or Firm*—Dority & Manning, P.A.

(57) ABSTRACT

An absorbent article includes a particulate chemical mixture, which is exothermically reactive in the presence of air or moisture, for heating at least a portion of the absorbent article. The heat generated improves the absorption of body fluids by lowering the viscosity of the absorbed fluids. The absorbent article can be formed as a sanitary napkin.

18 Claims, 2 Drawing Sheets

U.S. PATENT DOCUMENTS

| | | | |
|---|---|---|---|
| 5,300,103 A | 4/1994 | Stempel et al. | 607/108 |
| 5,366,491 A | 11/1994 | Ingram et al. | 607/108 |
| 5,425,975 A | 6/1995 | Koiso et al. | 428/74 |
| 5,431,622 A | 7/1995 | Pyrozyk et al. | 602/2 |
| 5,456,704 A | 10/1995 | Kilcullen | 607/111 |
| 5,468,236 A * | 11/1995 | Everhart et al. | 604/361.2 |
| 5,476,490 A | 12/1995 | Silver | 607/108 |
| 5,494,598 A | 2/1996 | Hughes | 252/70 |
| 5,599,336 A * | 2/1997 | Plischke | 604/368 |
| D380,051 S | 6/1997 | Davis et al. | D24/206 |
| 5,649,914 A | 7/1997 | Glaug et al. | 604/361 |
| 5,674,270 A | 10/1997 | Viltro et al. | 607/112 |
| 5,702,375 A | 12/1997 | Angelillo et al. | 604/358 |
| 5,728,125 A * | 3/1998 | Salinas | 604/361.2 |
| D407,823 S | 4/1999 | Davis et al. | D24/206 |
| 6,096,067 A * | 8/2000 | Cramer et al. | 607/108.2 |
| 6,099,556 A * | 8/2000 | Usui | 607/114.2 |
| 6,248,125 B1 * | 6/2001 | Helming | 607/108 |
| 6,265,631 B1 * | 7/2001 | Angelillo et al. | 602/2 |
| 6,320,095 B1 * | 11/2001 | Wall | 602/2 |
| 2001/0018605 A1 * | 8/2001 | Helming | 607/108 |

* cited by examiner

INTERNALLY HEATED ABSORBENT ARTICLE

CROSS-REFERENCE TO RELATED APPLICATIONS

This application is a divisional of application Ser. No. 09/133,438 filed Aug. 13, 1998 now abandoned, which, in turn, is a continuation-in-part of abandoned application Ser. No. 08/854,876 filed May 12, 1997, which, in turn, claims benefit of U.S. Ser. No. 60/033,987 filed Dec. 30, 1996, the disclosures of all of which are incorporated herein by reference in their entireties.

FIELD OF THE INVENTION

The present invention relates generally to an absorbent article, and particularly to an absorbent article having a mixture that generates heat when exposed to air and/or moisture.

BACKGROUND OF THE INVENTION

All manner and variety of devices or appliances configured for absorption of body fluids, such as menses, are well known. Sanitary napkins are the most frequently used of these devices. The prior art is replete with patents relating to protective pads and sanitary napkins for the absorption of body fluids and protecting the undergarment from staining. It has been suggested that from 20–25 percent of all sanitary napkins leak. A contributing factor to the leakage is that menses is a viscous fluid having aqueous and mucus-like components.

A problem in the performance of the absorbent is that the more viscous the material the slower the rate of absorption. Basically, the low viscous materials readily pass through the cover of the sanitary napkin and are absorbed by the absorbent. The higher viscosity materials in the menses may not be absorbed and can remain on the cover. Alternatively, the higher viscosity materials may be absorbed but remain at or near the point of insult occluding absorption of the lower viscosity materials. This limits the effectiveness of the absorbent and the utilization of the absorbent capacity of the sanitary napkin. Moreover, the absorbent may contain superabsorbent materials which preferentially absorb the aqueous constituents from low viscous materials thereby increasing the viscosity of the remaining material. This exacerbates the problem of the absorbent to absorb the viscous components of the menses.

Until now, surfactants have been used to improve the absorption of body fluids. One or more of the materials used in constructing the sanitary napkin, such as the cover and/or absorbent, have been treated to improve the material wettability. The problem of using a surfactant is that the surface energy of the coated material is modified but the surfactant does not appreciably modify, if at all, the viscosity of the body fluid. Thus, the higher viscosity materials are still not efficiently absorbed.

Accordingly, there is a need for an absorbent article, such as a sanitary napkin, which can modify the viscosity of a viscous material so that it can be absorbed.

SUMMARY OF THE INVENTION

This invention contemplates adult feminine hygiene articles for absorbing body fluids from a wearer and comprises a liquid permeable cover; a liquid-impermeable baffle; an absorbent enclosed between the cover and the baffle; and heat cell material as an integral part of the adult feminine hygiene article, for heating the absorbent, the heat cell material being free to receive menses from outside the adult feminine hygiene article, the heat cell material being reactable with menses to generate heat such that, in use, heat is generated when menses from the wearer is received at the adult feminine hygiene article, the heat being effective to lower the viscosity of the menses, thereby increasing the capability of the adult feminine hygiene article to absorb the resulting lower-viscosity menses. The adult feminine hygiene article has a liquid absorption capacity of about 1 milliliter up to about 30 milliliters.

In some embodiments of the invention, the heat cell material of the adult feminine hygiene article comprises a chemical mixture distributed throughout the absorbent, the chemical mixture being reactable in the presence of aqueous liquid to generate heat. The chemical mixture can be distributed randomly or substantially uniformly at multiple locations throughout the absorbent.

In some embodiments, the absorbent includes superabsorbent materials which absorb aqueous constituents from lower viscosity materials.

In some embodiments, the heating apparatus includes an air and moisture-permeable material enveloping the heat cell material.

DETAILED DESCRIPTION OF THE PREFERRED EMBODIMENTS

While the specification concludes with claims particularly pointing out and distinctly claiming that which is regarded as the invention, it is believed that the invention can be more readily understood with reference to the accompanying drawings of figures in conjunction with the following detailed description of the invention.

Figure 1:
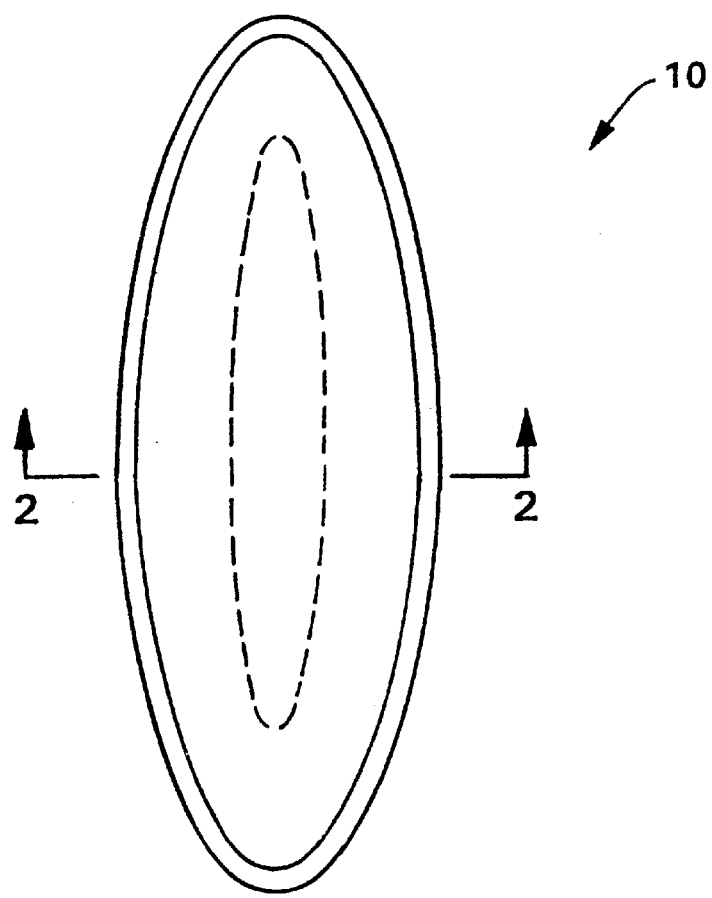
FIG. 1 is a top view of one embodiment of the absorbent article of the present invention.
Figure 2:
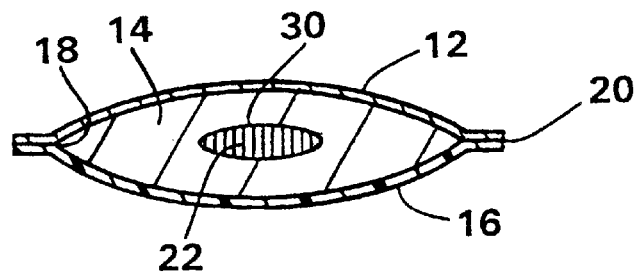
FIG. 2 is a transverse cross-sectional view of FIG. 1 along lines 2—2.
Figure 3:
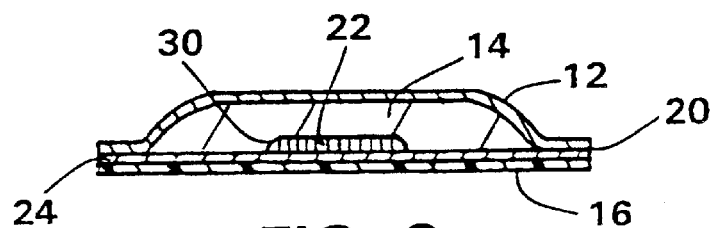
FIG. 3 is a transverse cross-sectional view of an alternative embodiment of the present invention.
Figure 4:
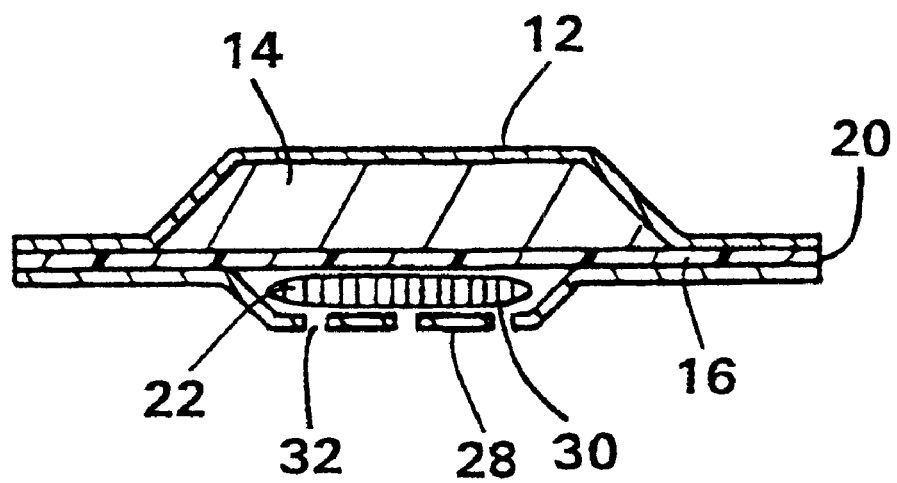
FIG. 4 is a transverse cross-sectional view of an alternative embodiment of the present invention.
Figure 5:
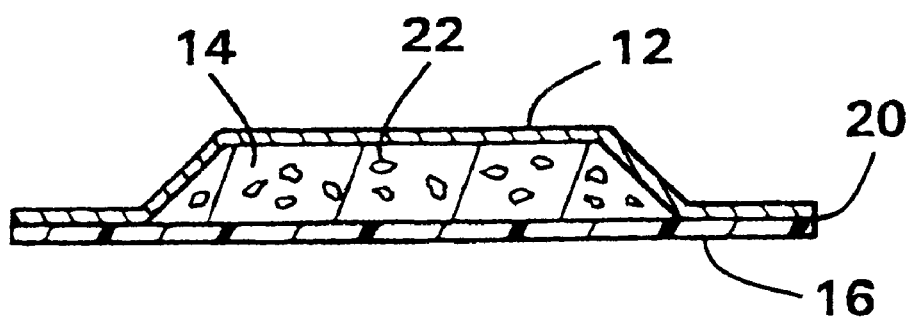
FIG. 5 is a transverse cross-sectional view of an alternative embodiment of the present invention.

Referring to FIGS. 1–5 of the drawings, in which like parts are identified with like reference characters. FIG. 1 illustrates a top view of a sanitary napkin 10 in accordance with this invention. As shown in these drawings and viewed from the top. i.e., that side which would normally be placed adjacent to the wearer during use, the sanitary napkin 10 is comprised of a fluid permeable cover 12 having first and second opposing surfaces; an absorbent layer 14 having first and second opposing surfaces, the absorbent layer generally being narrower than the cover 12; and a liquid-impervious backing or baffle 16 having first and second opposing surfaces. As seen in FIGS. 2 and 4, fluid permeable cover 12 and liquid-impervious baffle 16 extend beyond an edge 18 of absorbent 14 to enclose the absorbent and to define the perimeter 20 of the sanitary napkin 10. A first surface of fluid permeable cover 12 comprises the outermost top layer of sanitary napkin 10 and generally contacts or is positioned adjacent the body of a wearer when the napkin is utilized. A first surface on a top side of absorbent 14 is in surface-to-surface contact with a second opposing surface on the bottom side of fluid permeable cover 12. A second surface on a bottom side of absorbent 14 generally is in surface-to-surface contact with a first surface on a top side of liquid-impermeable baffle 16. Baffle 16 acts as a barrier by preventing liquid contained in absorbent 14 from passing through to clothing of a wearer adjacent second surface of the baffle. The second surface on the bottom side of baffle 16 generally comprises the outermost layer of sanitary napkin 10 as shown in the embodiments of FIGS. 2, 3 and 5. In these embodiments, the second surface of baffle 16 generally contacts or is positioned adjacent clothing of the wearer during use of sanitary napkin 10. As shown in FIG. 2, outer portions of the first surface of liquid-impermeable baffle 16 and outer portions of the second surface of fluid permeable cover 12 can be secured in surface-to-surface relationship about absorbent 14.

As used herein "edge" or "edge of the absorbent" are equivalent and encompasses the border at which the absorbent 14 terminates, without limitation to longitudinal sides or transverse ends of the absorbent 14 unless specifically so stated. Although not shown, one skilled in the art would understand that cover 12, absorbent 14, and baffle 16 can have a coterminous edge, but this is not preferred. Cover 12 and baffle 16 may be sealed together using any suitable means that will not leave a hard, uncomfortable residue that may be annoying to the wearer. As used herein, the term "sealed" encompasses configurations whereby fluid permeable cover 12 is directly joined to baffle 16 or, alternatively, by affixing fluid permeable cover 12 to an intermediate member, not shown, which may in turn be affixed to liquid-impermeable baffle 16. Methods for attaching cover 12 and baffle 16 are well known to those skilled in the art and include the use of hot melt adhesive, pressure sensitive adhesive, construction adhesive, double-sided tape, heat sealing and ultrasonic bonding.

As used herein, the term "sanitary napkin" refers to an article which is worn by females adjacent to the pudendal region and which is intended to absorb and contain various exudates which are discharged from the body such as blood, menses, and urine, and which is intended to be discarded when soiled, not laundered and reused. Interlabial devices which reside partially within and partially external of the female wearer's vestibule are also within the scope of this invention.

The sanitary napkin 10 further includes a heating apparatus 22 positioned below the cover 12 and preferably adjacent to the absorbent 14. The heating apparatus 22 can be comprised of one or more cells containing exothermic or electrochemical reactants that will produce heat when activated by oxygen or moisture or can comprise a material that will effectively distribute heat from the wearer's own body. Desirably, the heating apparatus 22 lowers the viscosity of the more viscous components of the menses allowing greater fluid mobility and thereby obtaining greater utilization of the absorbent capacity. When exothermic or electrochemical reactants are used, the heating apparatus 22 should generate enough heat to produce a temperature of from about 22° C. to about 55° C. More preferably, the heating apparatus 22 generates enough heat to produce a temperature of from about 27.5° C. to about 45° C. and most preferably, the heating apparatus 22 generates enough heat to produce a temperature of from about 27.5° C. to about 37° C.

Absorbent 14 can have the above thicknesses, lengths, and widths such that the absorbent has a liquid capacity from about 1 milliliter to about 100 milliliters of liquid. In preferred embodiments, absorbent 14 can retain at least about 5 milliliters of liquid, more preferably from about 5 milliliters to about 30 milliliters of liquid. The capacity of absorbent 14 and especially the use of heating means 22, enable sanitary napkin 10 to function efficiently in receiving and retaining blood, menses, and urine.

Referring to FIG. 3 the sanitary napkin, 10 can further include one or more additional layers 24 that are designed to enhance, modify or transfer fluid in a preferential manner. Such layers include cellulosic and polymeric materials such as tissue, superabsorbents and melt blown materials. Such layers and materials are commercially available from several sources and are well known to those skilled in construction of disposable absorbent articles, such as sanitary napkins, diapers and incontinent devices. The sanitary napkin 10 can also include shape conforming members adapted to contort and conform the sanitary napkin 10 to a wearer's anatomy during use.

Cover 12 is designed to contact the body of the wearer and therefore should be easily penetrated by body fluids. Thus cover 12 forms an outer surface of sanitary napkin 10. Cover 12 should also be non-irritating to the wearer's skin and preferably, will dot absorb an appreciable amount of fluid insulting its surface. The cover 12 can be constructed of a woven or nonwoven, natural or synthetic material. Suitable materials include bonded carded webs of polyester, polypropylene, polyethylene, nylon, or other heat-bondable fibers. Other polyolefins, such as copolymers of polypropylene and polyethylene, linear low-density polyethylene, finely-perforated film webs and net material, also work well. Particularly preferred are composite materials of a polymer and a nonwoven fabric material. Still another cover material is a spunbond web of polypropylene. The web can contain about 1% to about 6% titanium dioxide pigment to give it a clean, white appearance. A uniform spunbond material is desirable because it has sufficient strength in the longitudinal direction, even after being perforated, to resist being torn or pulled apart during use. The most preferred polypropylene webs have a basis weight of between about 10 and about 40 grams per square meter. An optimum basis weight is between about 12 and about 30 grams per square meter.

To aid in the penetration of the liquid through the web, the cover 12 can also be treated with a surfactant to improve its hydrophilic characteristics. The surfactant can include topical additions or internally applied materials like polysiloxanes.

Positioned adjacent to the cover 12 is the absorbent 14. As shown in FIGS. 2–5, cover 12 is in surface-to-surface contact with absorbent 14. The materials used in the absorbent 14 are designed to absorb body exudates, including menstrual fluids, blood and urine. Suitable materials include wood pulp fluff, rayon, cotton and meltblown polymer, such as polyester, polypropylene or coform. Coform is an airformed combination of meltblown polymers, such as polypropylene, and absorbent fibers. The absorbent 14 may be a composite comprised of a hydrophilic material that can be formed from various natural or synthetic fibers, wood pulp fibers, regenerated cellulose or cotton fibers, an airlaid tissue or a blend of pulp and other fibers. The absorbent 14 can be made from other well known materials used in absorbent articles, including multiple layers of cellulose wadding, cellulose sponge, hydrophilic synthetic sponge, such as polyurethane, and the like. The capacity of the absorbent 14 may be varied depending upon the intended usage of the final product.

Liquid-impervious baffle 16 acts as a barrier between the absorbed body fluids contained in the absorbent 14 and the person wearing the sanitary napkin 10. Accordingly, baffle 16 is nonabsorbent and impervious to liquids. To be impervious to liquids, baffle 16 must be free from apertures as shown in FIGS. 1–5. In this manner, baffle 16 prevents liquid from flowing therethrough and reaching the undergarments or clothing of a user of feminine napkin 10. Baffle 16 should be soft and compliant since a portion of baffle 16 may reside adjacent the thigh region of the wearer. As used herein, the term "compliant" refers to materials which will readily conform to the general external shape and contours of the human anatomy.

In a preferred embodiment, baffle 16 may permit the passage of air or vapor out of sanitary napkin 10 while blocking the passage of liquids from absorbent 14.

A good material for baffle 16 is a micro-embossed, polymeric film, such as polyethylene or polypropylene having a thickness in the range of from about 0.012 mm to about 1.0 mm. Bicomponent films can also be used as well as woven and nonwoven fabrics which have been treated to render them liquid-impermeable.

Referring to FIGS. 1 and 2, heating apparatus 22 is positioned beneath the cover 12 and intermediate absorbent 14. The heating apparatus 22 can include a chemical mixture enveloped in an appropriate air and moisture-permeable material 30. The material 30 can be a synthetic or natural, woven or nonwoven material. Desirably, the material 30 is capable of permitting air and moisture to pass while retaining the particulate chemical mixture. Non-limiting examples of such materials include a polyester nonwoven and a nonwoven spunbond polypropylene. Natural materials are also suitable for use in containing the chemical mixture. Cotton is an example of a natural material suitable for enveloping the chemical mixture.

The exothermic agents which can be utilized in the present invention may be a material which easily reacts with oxygen in the air, water from absorbed menses or both to generate heat at the time of reaction. When heating apparatus 22 generates heat by an exothermic reaction with oxygen, it is necessary that the reactants have an exchange of air. Although not particularly limited hereto, the reactants can be a mixture of an oxidizable substances such as iron, reduced iron, nickel, sodium sulfide and/or sodium sulfite; an oxidation accelerator and catalyst such as sodium chloride, calcium chloride, magnesium chloride, activated carbon, carbon powder and a mixture consisting of copper compound, manganese as well as a water retaining agent such as woodmeal or pulp powder. Other exothermic reactants are described in U.S. Pat. Nos. 4,331,731 and 4,573,447 the entire disclosures of which are incorporated herein by reference.

For example, the chemical mixture of heating apparatus 22 can include an intermediate having 30 weight percent vermiculite, 55 weight percent of an aqueous solution having 10 weight percent sodium chloride and 15 weight percent carbon of fine particle size. The intermediate is combined with a fine iron powder at a ratio of about 1:1. Iron powder is preferred because it reacts readily with the oxygen in the air in the presence of moisture to generate heat. Moreover, the material is a good thermal conductor allowing for uniformity of temperature distribution and avoiding localized areas of sensible heat. The fineness of the powder can be varied to change the rate of the reaction and thereby the amount of heat generated. As a general rule, the greater the amount of metal powder, the hotter the reaction.

Sodium chloride is used to catalyze the oxidation of the iron. It is particularly desirable in that it is readily available and inexpensive. However, the sodium chloride can be replaced with other suitable chlorides and sulfates, such as potassium chloride, calcium chloride, magnesium chloride, ferric sulfate, potassium sulfate, sodium sulfate, and magnesium sulfate.

Those skilled in the art will understand that the ratios of the components, particle size, and ingredient quality of the chemical mixture can be varied substantially to make either a hotter or cooler reaction mixture.

The chemical reaction which takes place in heating apparatus 22 of the present invention is an electrochemical reaction that is activated by water. No water or liquids are present in the absorbent article before use by a wearer. Thus, no heat is generated until liquid from the body of a wearer of sanitary napkin 10 is received. The electrochemical reaction generates heat by using an electrochemically active reducible element and an electrochemically active oxidizable element. The reducible element can be formed from an air depolarized cathode on which another material such as oxygen is reduced. The oxidizable element can be a foil material made from aluminum or magnesium or an alloy of both. The reducible element and oxidizable element are separated by a water absorbing material such as felt. Preferably, an electrolyte forming salt is incorporated in a dry granulated form with or adjacent to the reducible element to thereby avoid the need to impregnate the water absorbing material. This allows the heating apparatus 22 to have an extended storage life. Desirably, the electrolyte salt is applied uniformly into the cathode or reducible element. In the case of an air depolarized cathode using activated carbon or manganese dioxide, the table salt is originally uniformly dry mixed with the activated carbon or manganese dioxide in the range of about one to two and a half grams of salt to about one gram of carbon. Preferably, the ratio is from about one and a half grams of salt to one gram of carbon or manganese dioxide.

Heating apparatus 22 may be composed of a material that will effectively distribute heat from the wearer's body in absorbent 14. Desirably, such materials have a high thermal conductivity relative to absorbent 14. Thermal conductivity of a substance is readily ascertainable using well known techniques.

Referring to FIG. 3, a transverse cross-section of an alternative embodiment of the invention is illustrated. The heating apparatus 22 is positioned between the absorbent 14 and the baffle 16 so that the top of the heating apparatus 22 is adjacent to the absorbent 14 and the bottom of the heating apparatus is adjacent to the baffle 16. The heating apparatus 22 is similar to that described above for FIGS. 1 and 2, in that the chemical mixture comprising the heating apparatus 22 is surrounded by an enveloping material 30. As shown in FIG. 3, additional layer 24 has a first surface in surface-to-surface relationship with second surface of absorbent 14, heating apparatus 22 and outer portions of a second surface of cover 12. A second opposing surface of additional layer is in surface-to-surface relationship with the first surface of baffle 16. Thus additional layer 24 forms an intermediate layer between cover 12 and baffle 16.

Referring to FIG. 4, a transverse cross-section of an alternative embodiment of the invention is illustrated. Heating apparatus 22 is positioned between baffle 16 and a retaining layer 28 positioned below the baffle 16. Baffle 16 and retaining layer 28 are at least partially secured together in surface-to-surface relationship about at least outer portions and at perimeter 20 to enclose heating apparatus 22. In this embodiment, although it is preferred for the chemical mixture to be enveloped in the material 30 it is not necessary. Retaining layer 28 can be composed of a material similar to baffle 16. Desirably, retaining layer 28 is composed of an air permeable material, such as spunbond, an apertured film and the like. Retaining layer 28 can include one or more apertures or perforations 32 that will enhance the exchange of oxygen irrespective of the air permeability of the retaining layer 28 composition. Desirably, apertures or perforations 32 are positioned on the garment-facing surface of the retaining layer 28. The apertures or perforations 32 should be appropriately sized so that the chemical mixture does not escape if an enveloping material 30 is not used but still permit the interchange of air through the material.

Perforations 32 are necessary when the material is impermeable to the exchange of air such as when a polyolefin film is used.

Perforations can be made in many different ways, including cutting, needling, punching and the like. In some cases the perforations 32 can be arranged in a narrow area or strip of the retaining layer 28 as opposed to having the perforations distributed throughout the retaining layer 28. By having the perforations 32 arranged along a narrow strip, it is possible to slow the dissipation of moisture through the material and out of the chemical mixture. This can provide for a conservation of moisture within the chemical mixture, thereby increasing the life of the chemical mixture.

Referring to FIG. 5, a transverse cross-section of an alternative embodiment of the invention is illustrated. The chemical mixture of the heating apparatus 22 can be randomly or evenly distributed or located in multiple discrete identifiable pockets or areas similar to that described above for FIGS. 1–4, but with lesser amounts of the chemical mixture contained in each pocket. As shown in FIG. 5, the chemical mixture 22 is positioned at multiple locations throughout absorbent 14. As described earlier, the chemical mixture can be surrounded by an enveloping material 30. Otherwise, the chemical mixture can be spread apart and even break containment inside sanitary napkin 10. The chemical mixture can be distributed substantially uniformly throughout the absorbent whereby elements of the absorbent are disposed between respective ones of the discrete pockets of heat cell material.

While the invention has been described with reference to several preferred embodiments and illustrated with regard to a range of optional features, those skilled in the art will appreciate that various substitutions, omissions, modifications, and changes may be made without departing from the spirit hereof. Accordingly, it is intended that the foregoing description be deemed exemplary of the preferred scope of the present invention and not deemed a limitation thereof.

I claim:

1. An adult feminine hygiene article for absorbing menses, said adult feminine hygiene article comprising:
   a) a liquid permeable cover;
   b) a liquid-impermeable baffle;
   c) an absorbent between said cover and said baffle; and
   d) heat cell material as an integral part of said adult feminine hygiene article, said heat cell material being free to receive menses from outside said adult feminine hygiene article, said heat cell material being reactable with menses to produce a temperature of about 27.5° C. to about 45° C., such that, in use, heat is generated when menses is received at the adult feminine hygiene article, the heat being effective to lower the viscosity of the menses, thereby increasing a capability of the adult feminine hygiene article to absorb the resulting lower-viscosity menses, said adult feminine hygiene article having a liquid absorption capacity in an amount of about 1 milliliter up to about 30 milliliters.

2. The adult feminine hygiene article of claim 1 wherein said heat cell material is positioned substantially intermediate said absorbent.

3. The adult feminine hygiene article of claim 1 wherein said heat cell material is distributed substantially uniformly throughout said absorbent.

4. The adult feminine hygiene article of claim 1 wherein said absorbent includes superabsorbent materials which absorb aqueous constituents from low viscous materials.

5. The adult feminine hygiene article of claim 1 wherein said sanitary napkin does not contain any liquid before use of said adult feminine hygiene article.

6. The adult feminine hygiene article of claim 1 where said absorbent has a thickness from about 5 millimeters to about 25 millimeters.

7. The adult feminine hygiene article as in claim 1 wherein said heat cell material is distributed throughout said absorbent.

8. The adult feminine hygiene article as in claim 1 wherein said heat cell material is distributed randomly in multiple discrete pockets throughout said absorbent and whereby elements of the absorbent are disposed between respective ones of the discrete pockets of heat cell material.

9. The adult feminine hygiene article as in claim 1 wherein said heat cell material is enveloped in an air and moisture-permeable material.

10. A sanitary napkin for absorbing menses, said sanitary napkin comprising:
    a) a liquid permeable cover;
    b) a liquid-impermeable baffle;
    c) an absorbent between said cover and said baffle; and
    d) heat cell material as an integral part of said sanitary napkin, said heat cell material being free to receive menses from outside said sanitary napkin, said heat cell material being reactable with menses to produce a temperature of about 27.5° C. to about 45° C., such that, in use, heat is generated when menses is received at the sanitary napkin, the heat being effective to lower the viscosity of the menses, thereby increasing a capability of the sanitary napkin to absorb the resulting lower-viscosity menses, said sanitary napkin having a liquid absorption capacity in an amount of about 1 milliliter up to about 30 milliliters.

11. The sanitary napkin of claim 10 wherein said heat cell material is positioned substantially intermediate absorbent.

12. The sanitary napkin of claim 10 wherein said heat cell material is distributed substantially uniformly throughout said absorbent.

13. The sanitary napkin of claim 10 wherein said absorbent includes superabsorbent materials which absorb aqueous constituents from low viscous materials.

14. The sanitary napkin of claim 10 wherein said sanitary napkin does not contain any liquid before use of said sanitary napkin.

15. The sanitary napkin of claim 10 wherein said absorbent has a thickness from about 5 millimeters to about 25 millimeters.

16. The sanitary napkin as in claim 10 wherein said heat cell material is distributed throughout said absorbent.

17. The sanitary napkin as in claim 10 wherein said heat cell material is distributed randomly in multiple discrete pockets throughout said absorbent and whereby elements of the absorbent are disposed between respective ones of the discrete pockets of heat cell material.

18. The sanitary napkin as in claim 10 wherein said heat cell material is enveloped in the air and moisture-permeable material.

* * * * *